United States Patent [19]

Ishizumi et al.

[11] 3,953,446

[45] Apr. 27, 1976

[54] PROCESS FOR PREPARING QUINAZOLINES

[75] Inventors: Kikuo Ishizumi, Toyonaka; Kazuo Mori, Kobe; Michihiro Yamamoto, Nishinomiya; Masao Koshiba, Amagasaki; Shigeho Inaba, Takarazuka; Hisao Yamamoto, Nishinomiya, all of Japan

[73] Assignee: Sumitomo Chemical Company, Limited, Osaka, Japan

[22] Filed: Aug. 5, 1974

[21] Appl. No.: 494,885

[30] Foreign Application Priority Data
Aug. 20, 1973 Japan.............................. 48-93678

[52] U.S. Cl. .................. 260/251 QB; 260/256.4 Q; 260/295 B; 260/326.13 R; 260/349; 424/251
[51] Int. Cl.².............. C07D 239/82; C07D 405/04; C07D 405/06; C07D 409/06
[58] Field of Search................. 260/256.4 Q, 251 Q, 260/251 B

[56] References Cited

UNITED STATES PATENTS

| | | | |
|---|---|---|---|
| 3,712,892 | 1/1973 | Inaba et al.................... | 260/251 QB |
| 3,812,118 | 5/1974 | Yamamoto et al. ......... | 260/256.4 Q |
| 3,859,237 | 1/1975 | Inaba et al.................... | 260/251 QB |
| B252,947 | 1/1975 | Inaba et al.................... | 260/251 QB |

OTHER PUBLICATIONS

Banthorpe, "The Chemistry of the Azido Group," 1971, pp. 402–403, Interscience publishers.
Abramovitch, "Organic Reactive Intermediates," 1973, pp. 129–131, Academic Press.

*Primary Examiner*—Alton D. Rollins
*Assistant Examiner*—David E. Wheeler
*Attorney, Agent, or Firm*—Stevens, Davis, Miller & Mosher

[57] ABSTRACT

Quinazoline derivatives which have anti-inflammatory, antiviral, uricosuric activities are prepared by reacting an indole-2-carbonylazide derivative with an oxidizing agent under mild conditions.

2 Claims, No Drawings

PROCESS FOR PREPARING QUINAZOLINES

The present invention relates to a novel method for preparing quinazolinone derivatives.

More particularly, the present invention relates to a novel method for preparing quinazolinone derivatives represented by the general formula,

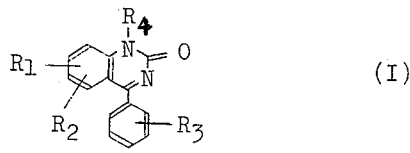

wherein $R_1$, $R_2$ and $R_3$ are independently a hydrogen or halogen atom, a trifluoromethyl, nitro, $C_1$–$C_4$ alkylsulfonyl, $C_1$–$C_4$ alkyl, $C_1$–$C_4$ alkoxy or $C_1$–$C_4$ alkylthio group, and $R_4$ is a hydrogen atom, a $C_1$–$C_4$ alkyl, aralkyl, $C_1$–$C_4$ alkanoyloxy-$C_1$–$C_4$ alkyl, $C_1$–$C_4$ alkoxy-$C_1$–$C_4$ alkyl, polyhalogeno $C_1$–$C_4$ alkyl, cyclo $C_3$–$C_6$ alkyl, cyclo-$C_3$–$C_6$ alkyl-$C_1$–$C_4$ alkyl, tetrahydrofurfuryl, tetrahydropyranylmethyl, pyridylmethyl, furylmethyl or thineylmethyl group.

The well-known methods for preparing the quinazolinone derivatives represented by the formula (I) are condensation of o-aminobenzophenone derivatives of the formula,

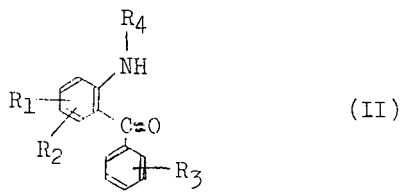

wherein $R_1$, $R_2$, $R_3$ and $R_4$ are as defined above, with, for example, urea or alkyl carbamate.

However, many of the o-aminobenzophenone derivatives (II) are in general difficult to obtain by synthesis, and particularly synthesis of the derivatives in which $R_4$ is various alkyl groups from ones in which $R_4$ is a hydrogen atom generally requires as many as three reaction steps, so that the derivatives (II) are very unsatisfactory as a starting material for preparation of quinazolinone derivatives. Furthermore the above-mentioned condensation reaction itself is disadvantageous in terms of a high temperature reaction in the presence of catalysts and a great difficulty of the treatment after reaction.

The inventors have found a very advantageous method for preparing the quinazolinone derivatives of the general formula (I), using, as a starting material, not o-aminobenzophenone derivatives (II) but indole derivatives easily obtainable by a synthetic method, and, in addition, by a reaction process in which severe reaction conditions were not necessary and the treatment after the reaction was easy.

An object of the present invention is to provide a method for preparing the quinazolinone derivatives of the formula (I) by reacting indole-2-carbonylazide derivatives of the formula,

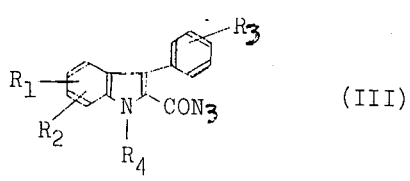

wherein $R_1$, $R_2$, $R_3$ and $R_4$ are as defined above, with an oxidizing agent.

The method of the present invention, therefore, includes a ring-enlargement reaction from an indole ring to a quinazoline ring which has not been known in the prior art nor expected from any literature.

The indole-2-carbonylazide derivatives of the formula (III) which are used as a starting material according to the present invention include new compounds and can easily be prepared by reacting corresponding indole-2-carboxylic halide derivatives with sodium azide.

The method of the present invention can be carried out by reacting the indole-2-carbonylazide derivatives of the formula (III) with an oxidizing agent. The oxidizing agents include ozone, hydrogen peroxide, peracids such as performic acid, peracetic acid and perbenzoic acid, chromic acid, halogen and hypohalite of sodium, potassium or calcium which are not of course limited thereto. The reaction can easily proceed at room temperature in a solvent in general, and, if necessary, may be carried out under cooling or heating. The solvents, which depend on the type of oxidizing agents, generally include water, chloroform, carbon tetrachloride, acetic acid, formic acid, acetone, an alcohol and tetrahydrofuran.

When $R_4$ in the indole-2-carbonylazide derivatives of the formula (III) means a hydrogen atom, oxamylazide derivatives of the formula,

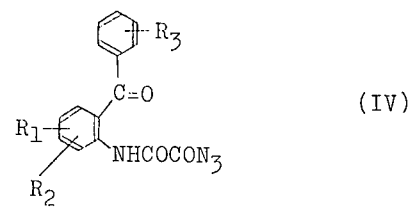

wherein $R_1$, $R_2$ and $R_3$ are as defined above, can be isolated as transient intermediates of the reaction depending upon the reaction conditions. The oxamylazide derivatives can be converted into the quinzolinone derivatives of the formula (I) by heating in the presence or absence of a solvent. As the solvents, there are used inert solvents such as benzene, toluene, carbon tetrachloride, pyridine and dimethylformamide. It is a matter of course that, even from the indole-2-carbonylazide derivatives of the formula (III) in which $R_4$ is a hydrogen atom, the quinazolinone derivatives of the formula (I) can directly be prepared without isolating the intermediate oxamylazide derivatives.

The quinazolinone derivatives of the formula (I) according to the present invention are very useful as anti-inflammatory agents, antiviral agents and uricosuric agents, and as an intermediate for preparing other superior anti-inflammatory agents and central nervous system depressants.

According to the present invention, the following quinazolinone derivatives can be obtained.

4-Phenyl-2(1H)-quinazolinone
4-Phenyl-6-chloro-2(1H)-quinazolinone
4-Pnenyl-6-fluoro-2(1H)-quinazolinone
4-Phenyl-6-methyl-2(1H)-quinazolinone  4-Phenyl-6-methoxy-2(1H)-quinazolinone
4-Phenyl-6-nitro-2(1H)-quinazolinone  4-Phenyl-6-trifluoromethyl-2(1H)-quinazolinone
4Phenyl-6,7-dimethoxy-2(1H)-quinazolinone
4-(o-Chlorophenyl)-6-nitro-2(1H)-quinazolinone 4-(o-Fluorophenyl)-6-chloro-2(1H)-quinazolinone
1-Methyl-4-phenyl-2(1H)-quinazolinone
1-Methyl-4-phenyl-6-chloro-2(1H)-quinazolinone
1-Methyl-4-phenyl-6-iodo-2(1H)-quinazolinone
1-Methyl-4-phenyl-6-methoxy-2(1H)-quinazolinone
1-Methyl-4-phenyl-6-nitro-2(1H)-quinazolinone
1,6-Dimethyl-4-phenyl-2(1H)-quinazolinone
1-Ethyl-4-phenyl-6-nitro-2(1H)-quinazolinone
1-Ethyl-4-(o-tolyl)-6-chloro-2(1H)-quinazolinone
1-Isopropyl-4-phenyl-7-methyl-2(1H)-quinazolinone
1-Isopropyl-4-phenyl-6-methoxy-2(1H)-quinazolinone
1-Isopropyl-4-phenyl-6-nitro-2(1H)-quinazolinone
1-Isobutyl-4-phenyl-6-chloro-2(1H)-quinazolinone
1-n-Butyl-4-phenyl-6-nitro-2(1H)-quinazolinone
1-(2,2,2-Trifluoroethyl)-4-phenyl-6-chloro-2(1H)-quinazolinone
1-(2,2,3,3,3-Pentafluoropropyl)-4-phenyl-6-methyl-2(1H)-quinazolinone
1-Benzyl-4-phenyl-6-nitro-2(1H)-quinazolinone
1-Acetoxyethyl-4-phenyl-6-chloro-2(1H)-quinazolinone
1-Acetoxyethyl-4-phenyl-6-nitro-2(1H)-quinazolinone
1-Methoxyethyl-4-phenyl-6-chloro-2(1H)-quinazolinone
1-(2-Ethoxyethyl)-4-phenyl-6-nitro-2(1H)-quinazolinone
1-Cyclohexyl-4-phenyl-6-nitro-2(1H)-quinazolinone
1-Cyclopropylmethyl-4-phenyl-6-chloro-2(1H)-quinazolinone
1-Cyclopropylmethyl-4-(o-tolyl)-6-chloro-2(1H)-quinazolinone
1-Cyclopropylmethyl-4-phenyl-6-nitro-2(1H)-quinazolinone
1-Cyclopropylmethyl-4-phenyl-6-trifluoromethyl-2(1H)-quinazolinone
1-Cyclopropylmethyl-4-phenyl-6-methylsulfonyl-2(1H)-quinazolinone
1-Cyclopropylmethyl-4-phenyl-6-bromo-2(1H)-quinazolinone
1-Cyclopropylmethyl-4-phenyl-6,8-dichloro-2(1H)-quinazolinone
1-Cyclopropylmethyl-4-phenyl-6-methoxy-2(1H)-quinazolinone
1-Cyclopropylmethyl-4-(o-fluorophenyl)-6-chloro-2(1H)-quinazolinone
1-Cyclopropylmethyl-4-phenyl-6-methylthio-2(1H)-quinazolinone
1-Cyclohexylethyl-4-phenyl-6-chloro-2(1H)-quinazolinone
1-Cyclopropylmethyl-4-(o-chlorophenyl)-6-nitro-2(1H)-quinazolinone
1-Cyclopentylmethyl-4-phenyl-6-nitro-2(1H)-quinazolinone
1-Cyclohexylmethyl-4-phenyl-6-nitro-2(1H)-quinazolinone
1-Tetrahydrofurfuryl-4-phenyl-6-nitro-2(1H)-quinazolinone
1-(2-Tetrahydropyranylmethyl)-4-phenyl-6-nitro-2(1H)-quinazolinone
1-(2-Pyridylmethyl)-4-phenyl-6-nitro-2(1H)-quinazolinone
1-(2-Furylmethyl)-4-phenyl-6-nitro-2(1H)-quinazolinone
1-(2-Thienylmethyl)-4-phenyl-6-nitro-2(1H)-quinazolinone The present invention will be illustrated with reference to the following examples which are only given for the purpose of illustration and not to be interpreted as limiting.

EXAMPLE 1

A mixture of 2.0 g of 1-methyl-3-phenyl-5-chloroindole-2-carboxylic acid and 7.0 g of thionylchloride was heated under reflux for 1 hour. Thereafter, an excess of thionylchloride was distilled off under a reduced pressure, and residual carboxylic acid chloride was dissolved in 18 ml of acetone. To the acetone solution was added at a time a solution of 0.70 g of sodium azide in 2 ml of water with cooling and stirring. After stirring at room temperature for 1 hour, 18 ml of water was added thereto to separate crystals which were then filtered and washed successively with water and a 1 : 1 mixture of acetone and water. 1-Methyl-3-phenyl-5-chloroindole-2-carbonylazide thus obtained was immediately, without drying, suspended in 20 ml of acetic acid. To the suspension was added dropwise a solution of 2.0 g of chromic anhydride in 2 ml of water at below 17°C with stirring. The mixture was allowed to react at room temperature for 3 hours, and then 100 ml of water was added thereto to separate crystals which were then filtered. The crystals thus obtained were chromatographically refined on a column packed with 30 g of silica gel using ethylacetate as a solvent to obtain 1-methyl-4-phenyl-6-chloro-2(1H)-quinazolinone, m.p. 223.5 – 224.5°C.

EXAMPLE 2

A mixture of 1.0 g of 1-methyl-3-phenyl-5-nitroindole-2-carboxylic acid and 3 g of thionylchloride was heated under reflux for 1 hour. Thereafter, an excess of thionylchloride was distilled off under a reduced pressure, and the residue was suspended in 17 ml of acetone and then 0.5 ml of an aqueous solution containing 0.33 g of sodium azide was stirred therein with ice-cooling. After stirring at 6°C for 1 hour, 17 ml of water was added thereto to separate crystals which were then filtered and washed successively with water and a 1 : 1 mixture of acetone and water. 1-Methyl-3-phenyl-5-nitroindole-2-carbonylazide thus obtained was suspended, without drying, in 10 ml of acetic acid. To the suspension was added dropwise a solution of 1.0 g of chromic anhydride in 1 ml of water at 15° to 20°C with stirring. The mixture was allowed to react at room temperature for 3 hours, and then 50 ml of water was added thereto to separate crystals which were then filtered. The crystals thus obtained were 1-methyl-4-phenyl-6-nitro-2(1H)-quinazolinone, m.p. 261.5° – 264.5°C.

EXAMPLE 3

2.0 g of 3-(o-fluorophenyl)-5-chloroindole-2-carbonylazide was suspended in 20 ml of acetic acid and a solution of 2.0 g of chromic anhydride in 2 ml of water was added dropwise thereto at 15° to 20°C. The mixture was allowed to react at room temperature for 3 hours to obtain crystals of [2-(o-fluorobenzoyl)-4- chlorophenyl]-oxamylazide (m.p. 105° – 106°C). 0.10 g of the oxamylazide was suspended in 3 ml of toluene and heated under reflux for 6 hours. After cooling, the separated crystals were filtered and washed with ether to obtain 4-(o-fluorophenyl)-6-chloro-2(1H)-quinazolinone, m.p. above 300°C.

EXAMPLE 4

1.0 g of 1-methyl-3-phenyl-5-nitroindole-2-carbonylazide was suspended in 20 ml of acetic acid and then a mixed gas of ozone and oxygen was passed through the suspension at 15° to 20°C for 1.5 hours with stirring to obtain a complete solution. 50 ml of water was added thereto and the whole solution was extracted with ether. The separated ether layer was washed successively with an aqueous caustic soda solution and water, dried over anhydrous sodium sulfate and distilled under a reduced pressure. The residue thus obtained was washed with ether to obtain 1-methyl-4-phenyl-6-nitro-2(1H)-quinazolinone, m.p. 261° – 264°C.

What is claimed is:

1. A process for preparing a quinazolinone of the formula,

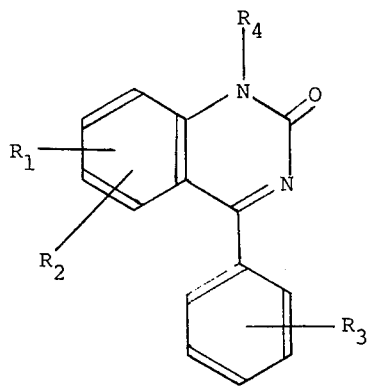

(I)

wherein $R_1$, $R_2$ and $R_3$ are independently a hydrogen atom, a halogen atom, a $C_1$-$C_4$ alkylsulfonyl group, a $C_1$-$C_4$ alkyl group provided that for $R_1$ and $R_2$ said alkyl group is a straight chain $C_1$-$C_4$ alkyl group, a $C_1$-$C_4$ alkoxy group or a $C_1$-$C_4$ alkylthio group; and $R_4$ is a hydrogen atom, a $C_1$-$C_4$ alkyl group, benzyl, a $C_1$-$C_4$ alkoxy-$C_1$-$C_4$ alkyl group, a polyhalo $C_1$-$C_4$ alkyl group, a cyclo $C_3$-$C_6$ alkyl group, a cyclo $C_3$-$C_6$ alkyl -$C_1$-$C_4$ alkyl group, a tetrahydrofurfuryl group, a furylmethyl group or a thienylmethyl group, which comprises the set of reacting an indole-2-carbonylazide of the formula,

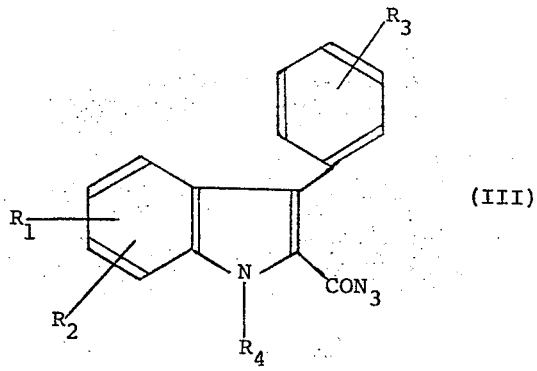

(III)

wherein $R_1$, $R_2$, $R_3$ and $R_4$ are as defined above, with an oxidizing agent selected from the group consisting of ozone, hydrogen peroxide, performic acid, peracetic acid, perbenzoic acid, chromic acid, halogen and hypohalite of sodium, potassium or calcium in the presence of a solvent.

2. A process according to claim 1, wherein the solvent is selected from the group consisting of water, chloroform, carbon tetrachloride, acetic acid, acetone, an alcohol and tetrahydrofuran.

* * * * *